(12) United States Patent
Salva Calcagno

(10) Patent No.: US 7,906,192 B2
(45) Date of Patent: Mar. 15, 2011

(54) NON-INTRUSIVE PORTABLE SAFETY SEAL USED TO OBTAIN PEOPLE'S DNA AND GENETIC PATTERNS THROUGH FINGERPRINTING

(76) Inventor: Eduardo Luis Salva Calcagno, Buenos Aires (AR)

( * ) Notice: Subject to any disclaimer, the term of this patent is extended or adjusted under 35 U.S.C. 154(b) by 744 days.

(21) Appl. No.: 11/919,512

(22) PCT Filed: Apr. 24, 2005

(86) PCT No.: PCT/US2005/014546
§ 371 (c)(1),
(2), (4) Date: Oct. 29, 2007

(87) PCT Pub. No.: WO2006/115499
PCT Pub. Date: Nov. 2, 2006

(65) Prior Publication Data
US 2009/0126625 A1    May 21, 2009

(51) Int. Cl.
*B32B 9/00* (2006.01)
*B32B 33/00* (2006.01)
*B32B 23/02* (2006.01)
*A61B 5/117* (2006.01)
*B42D 15/00* (2006.01)
*B41K 1/00* (2006.01)

(52) U.S. Cl. ...... 428/40.1; 428/41.7; 428/192; 428/194; 428/408; 427/1; 283/78; 118/31.5

(58) Field of Classification Search ................. 428/40.1, 428/40.2, 41.7, 121, 192, 194, 408, 915, 428/916; 427/1; 238/78; 118/31.5, 264, 118/269
See application file for complete search history.

(56) References Cited

U.S. PATENT DOCUMENTS

| 5,143,551 A | 9/1992 | Mason, Jr. et al. | 118/31.5 |
| 5,709,746 A | 1/1998 | Ballard | 118/31.5 |
| 6,659,038 B2 | 12/2003 | Salva Calcagno | 118/31.5 |

FOREIGN PATENT DOCUMENTS

WO    2005/115243    12/2005

*Primary Examiner* — Patricia L Nordmeyer
(74) *Attorney, Agent, or Firm* — Jacobson Holman PLLC

(57) ABSTRACT

A non-intrusive portable safety seal to collect human organic remnants in order to obtain DNA and genetic patterns of fingerprints is provided. The proposed seal comprises four related basic components: a sheet of paper or base forming a triptych, which serves to support the entire set, an adhesive-covered central sheet bearing a safety seal on the front surface, a two-surfaced sheet with adhesive on both surfaces and a graphite or granulated sheet adheres to it. In addition, the seal has two adhesive-covered safety flaps that protect the entire set. An alternative seal comprises a base sheet that is able to receive four fingerprints of four fingers, containing a fifth separation sheet between the graphite or granulated sheet and the two-surfaced adhesive layer.

11 Claims, 4 Drawing Sheets

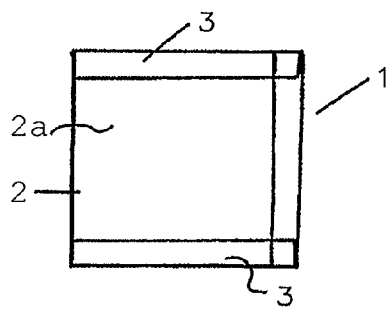
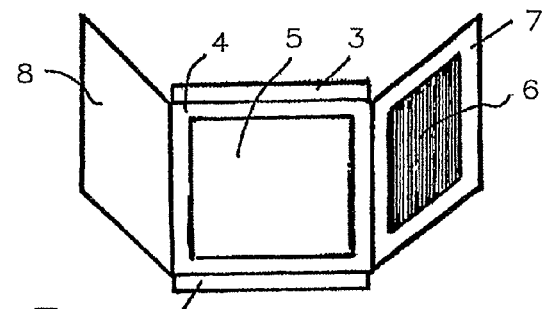
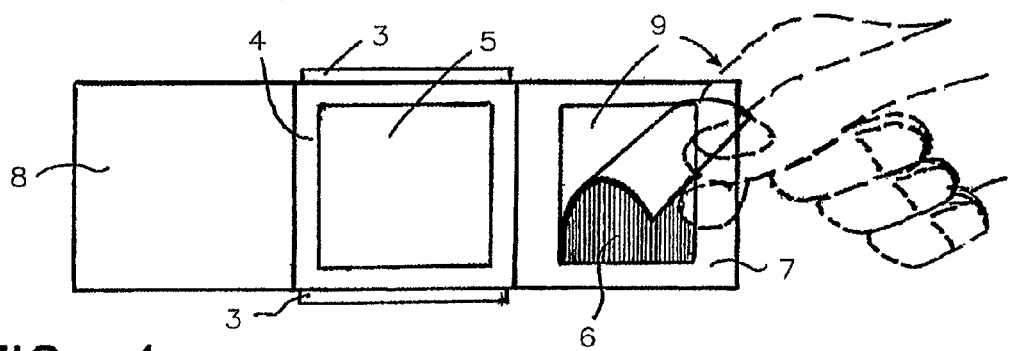
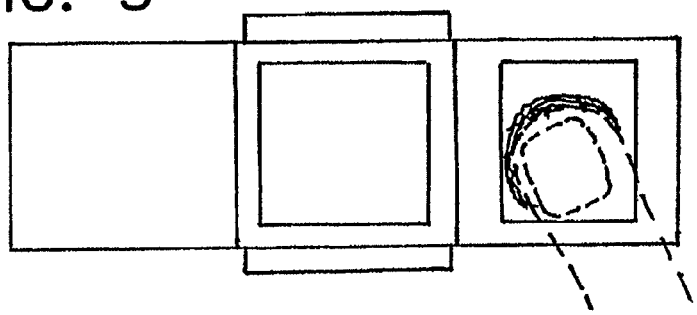

FIG. 6
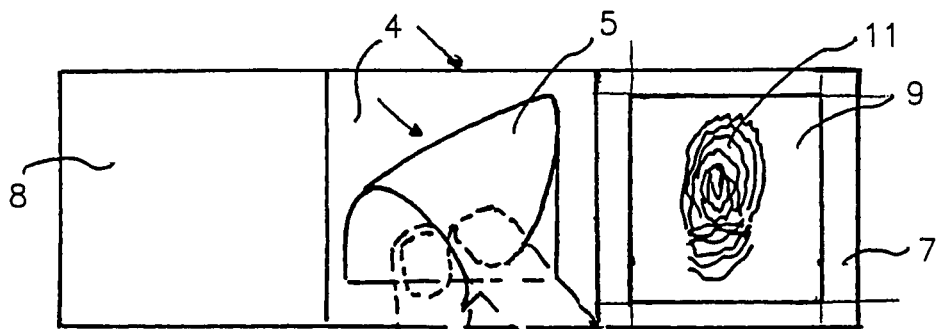
FIG. 10
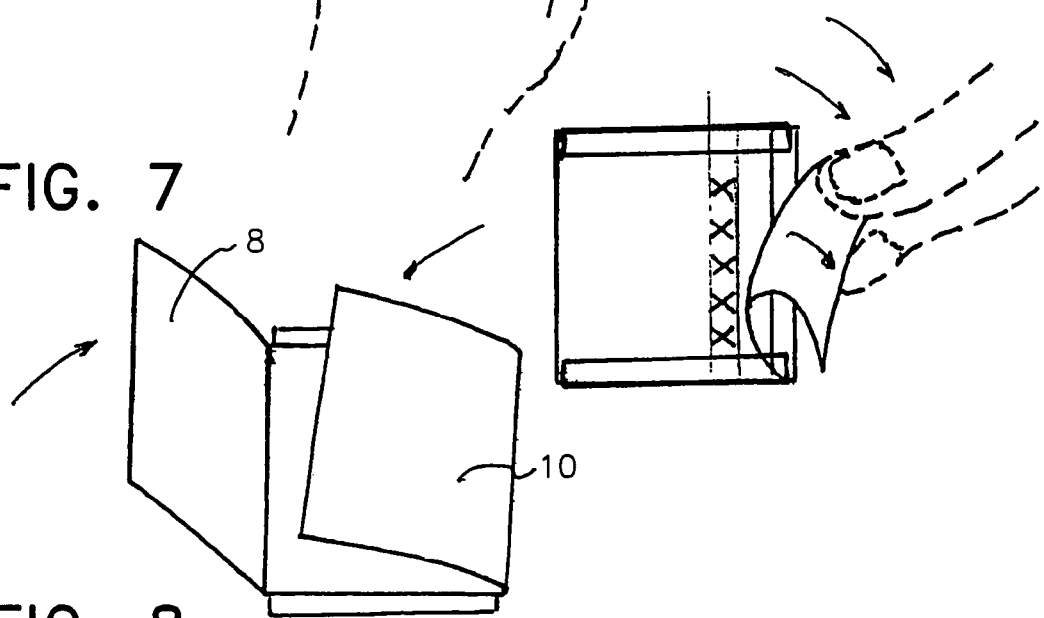
FIG. 7
FIG. 8
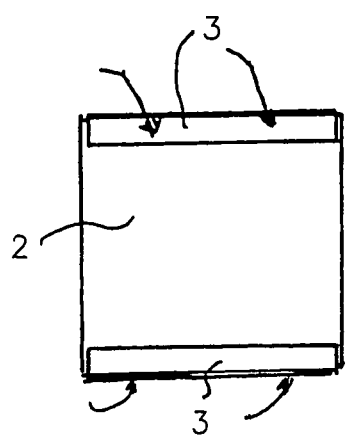
FIG. 9
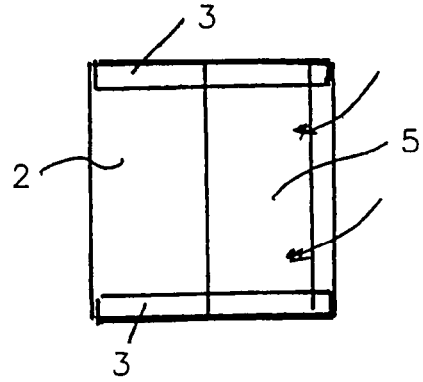

NON-INTRUSIVE PORTABLE SAFETY SEAL USED TO OBTAIN PEOPLE'S DNA AND GENETIC PATTERNS THROUGH FINGERPRINTING

BACKGROUND OF THE INVENTION

1. Field of the Invention

This invention relates to a non-intrusive portable safety seal to collect human organic residues in order to obtain DNA and genetic patterns from fingerprinting.

In addition, the invention has all the characteristics of a safety seal to stamp, record, or adhere people's imprints and their DNA. The invention provides a rapid, effective, and safe method for the accreditation of identities and genetic patterns. This is made possible by obtaining recordings of thumb imprints on the adhesive of the seal, as well as obtaining remnant particles of epithelial dead cells and organic residues (such as from the humidity and grease of the finger, etc.) bonded to the same adhesive or on the graphite or granulated sheets for testing the DNA by using certain reagents in an appropriate laboratory.

The non-intrusive characteristic of the present invention me that it is not necessary to compulsively introduce into the human body any strange elements to obtain DNA, as would be currently required when taking blood samples with syringes or when introducing swabs into the mouth to obtain DNA samples.

The proposed seal comprises four overlapped basic components: a sheet paper or base forming a triptych, which serves to support the entire set; an adhesive-covered central sheet bearing a safety seal on the front side; a two-faced sheet with double adhesive and a graphite or granulated sheet bonded to it. In addition, the stamp has two safety flaps that protect the entire set.

A double safety feature is achieved through the implementation of the seal: the person's fingerprint and DNA. The present invention is applicable to procedures to obtain genetic patterns and to preserve identities or to determine the forgery of identities.

2. Description of the Prior Art

It is known that U.S. Pat. No. 6,659,038 of the same applicant solves the problem of fingerprinting without the use of ink and introducing a graphite sheet.

The same applicant has filed another Argentinean patent application (No. P 04 01 01743, filed May 19, 2004) that reveals a safety seal sticker which includes graphite or a granulated sheet that provides a safety element to replace traditional fingerprints stained with ink on identity documents, cards, licenses, passports, commercial documents, etc. This application also provides a portable and alternative process to be used by police, scientific, judicial, forensic, or security forces, to facilitate people's identification on the street and to safely carry the fingerprint and DNA obtained.

The current invention utilizes this last method and proposes improvements as a safety seal intended to take fingerprints and DNA in public places or any other place.

Another purpose of this invention is to provide a portable safety seal that incorporates a graphite or granulated sheet for fingerprints and DNA, which presents a special configuration for this use because it introduces additional safety measures to avoid tampering and contributes to the adequate preservation of the collected genetic material from its collection and transportation until the final reception at the laboratory or site where its organic content will be analyzed.

SUMMARY OF THE INVENTION

The present invention, as previously explained, relates to a portable safety seal to stamp, record, or adhere people's fingerprints and their DNA, aimed to be a rapid, effective, non-intrusive, and safe method for the accreditation of identities. This is possible by recording of thumb imprints or any other finger on the adhesive of the seal, as well as obtaining the remnant particles of epithelial cells and organic residues (such as from the humidity and grease of the finger, etc.) that bond to the same adhesive and enabling the DNA to be tested with certain reagents in an appropriate laboratory.

The final product is highly functional, given the practical way to manipulate it. It is hygienic, given that the remnants of graphite disappear by slightly rubbing the surface impregnated with a simple tissue paper or bond paper or even by rubbing with another finger. It is safe because it neither produces allergies nor any kind of adverse reactions. It is economical and versatile because it adjusts to the different user's needs, according to different special or universal measures to be adopted for its final configuration (for only one fingerprint or for all 5 fingers, left or right, for example). Moreover, it provides safety and inviolable measures necessary for the fingerprints and DNA to be taken to the approved control agency, such as police, firemen, airports, hospitals, private laboratories, etc., where they will be processed in order to identify the person's identity.

A distinctive aspect to be highlighted in relation to the prior art is that once the portable safety seal was used according to the techniques and mechanisms herein explained, there is no need to keep the organic remnants and DNA at preservation temperatures in refrigerators, as is the case with DNA collected by traditional intrusive systems such as blood collected through syringes or swabs introduced into the person's mouth to collect saliva.

These two intrusive systems present, on one hand, the danger to contaminate the person who manipulates them, as is the case of blood collected with a syringe that may contain HIV. On the other hand, it is worthwhile noting that, upon obtaining DNA through intrusive methods, from the very moment when the blood or saliva is collected, it is exposed to the possibility that the person taking the sample may use these samples for other purposes, constituting a high risk of inappropriate use.

The great disadvantage of these traditional methods is that they allow the unduly or non-authorized use of the organic samples collected. Therefore, human DNA as an identification tool is currently a double-edged sword when present systems are able to manipulate genetic information taken for criminal purposes since the only thing that prevents a drop of blood or a sample of saliva from that collection to appear in other scenarios is the honesty of the person who has collected the sample and taken it to its final destination.

This requirement of the present technology can be satisfied with this invention, which provides an inviolable safety seal for obtaining and transporting genetic samples collected, making them impossible to manipulate at will.

It must be taken into account that epithelial cell manipulation can only be done at specialized laboratories, thus eliminating the risk of unduly using DNA incorporated in the seal. To obtain a genetic pattern from the epithelial cell sample, said cell has to undergo a process named "PCR" (polymerase multiplication) which consists in multiplying the same genetic patterns so as not to lose information and then to work with the genetic information so multiplied. This genetic information lady processed by the PCR technique cannot be manipulated in another scenario, since it is no longer the original source. It will also be impossible to remove cells from the adhesive-covered side of the seal since said cells will contain remnants of adhesives thereby providing evidence of its impurity and doubts to its origin.

This does not currently happen with blood or saliva, since these intrusive techniques allow one to manipulate DNA from its original phase, even enabling tampering or forging at its preservation site, where intentional changes to bottle or vial labels containing samples could be performed.

The undue use of or tampering of the samples would not be possible with the safety seal currently proposed. It must be highlighted that once the seal is used, it is hermetically sealed by a colored adhesive-covered sheet that contains the safety printing that reveals at first sight if it was broken or tampered with.

It is worth mentioning that every manufacture and production stage of the safety seal is carried out in a sterilized and contamination-free environment.

BRIEF DESCRIPTION OF THE DRAWINGS

FIG. 1 is a top plan view of the safety seal of this invention, closed, with unopened safety flaps, ready for use.

FIG. 2 is a front perspective view of the seal when opened, showing three parts of a triptych.

FIG. 3 is a top plan view of the completely opened seal, which shows how the graphite or granulated sheet should be detached.

FIG. 4 shows the details of a user rubbing his thumbs on the graphite or granulated sheet already detached from the seal.

FIG. 5 is a top plan view of a seal being used by a user wherein the user stamps a fingerprint on the lateral sheet with two-faced adhesive.

FIG. 6 represents a step in which a user detaches the central safety adhesive-covered sheet that will serve to close the set after the fingerprint is stamped on the seal.

FIG. 7 is a perspective view of a safety seal during the closing process in order to protect the fingerprint previously stamped.

FIG. 8 is a top plan view of the seal that shows how the seal closed by its safety flaps on its top and bottom edges appears.

FIG. 9 shows the last stage of the process, which consists of sticking the safety adhesive-covered sheet on the only opened lateral edge of the seal.

FIG. 10 shows a step in which attempts are made to remove or detach the safety sheet of the seal, once it has been sealed and the sheet bonded, leaving on sight the safety printing transferred to the visible frontal side of the set.

DESCRIPTION OF THE PREFERRED EMBODIMENTS

Figure 13:
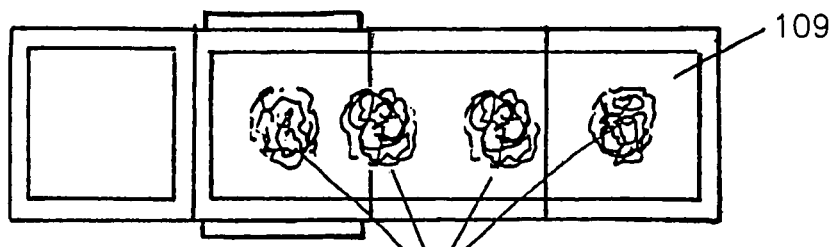
FIG. 13 shows a top plan view of the unfolded seal in its second embodiment, with four fingerprints already stamped.

When the user needs to identify a person through the seal proposed, the steps are as follows.

The seal is taken and the two safety flaps that close the top and bottom edges are detached. The main body of the triptych-configuration is opened and the graphite or granulated adhesive-covered sheet on one of the internal sides of the triptych is removed from the safety seal (FIG. 3).

Then, the finger of a subject from which the visible or latent printing needs to be obtained is selected. The print for the subject's fingerprint and DNA is visible if a graphite sheet is used or latent if a granulated sheet is used). Generally, the thumb is selected, although it could be any other finger. The selected finger is sufficiently rubbed on the detached graphite or granulated sheet (FIG. 4), such that the graphite of the graphite sheet is transferred to the selected finger, impregnating and covering most of the surface of the finger where the fingerprint is to be obtained.

Once the finger is impregnated with the dried graphite dust taken from the sheet, that finger is lightly pressed on the two-adhesive covered sheets that remained uncovered on one of the triptych sides where the graphite sheet was initially detached (FIG. 5).

The reaction produced between the wet adhesive and the dry graphite dust that is on the finger is as follows: The adhesive keeps the graphite dust attached to the surface of the external papillae (ridge) of the finger impregnated with graphite. When the finger is stamped and pressed on the adhesive-covered surface of the sheet, the drawing of the fingerprint will be stamped on the surface of the sheet. The fingerprint will be clear and visible in its original state without deformations. Such fingerprint identifies the person who stamped it according to the dactyloscopic system that classifies it, and to the organic remnants collected from the genetic patterns of the person's DNA.

In this way, the covering of the intermediate papilla grooves between ridges is prevented, as does sometimes occur with the wet or paste ink traditionally used to take fingerprints.

Once the fingerprint is collected, the main triptych body must be closed, for which the propylene adhesive-covered sheet on one side and attached to the central panel of said triptych must be detached (FIG. 6). This sheet can be easily distinguished since it is preferably presented in colors.

Then two lateral panels of the triptych (FIG. 7) are closed, which include the one that contains the fingerprint collected and the other one with space to manually fill in information concerning the person whose identity is to be verified. The two-surfaced adhesive-covered sheet (9) containing the fingerprint (11) will not stick to the central panel (4) when two lateral panels are folded one over the other, because said central panel (4) is treated by silicone and the adhesive of the sheet (9) cannot stick to the central panel (4). This structure perfectly preserves the fingerprint as well as genetic material collected.

Once the triptych is closed, the safety flaps of the top and bottom edge are bonded again (FIG. 8). The polypropylene safety adhesive-covered sheet previously detached is used as a seal to close the only lateral edge of the triptych that remains open (FIG. 9).

As said polypropylene sheet has adhesive on one side and the external surface of the triptych has no silicon, said polypropylene sheet will stick firmly to the non-silicone paper. If broken or detached, the seal could not be re-used because the statement on the seal indicating that it has been removed (FIG. 10) will be visible, as a result of the safety process through which a warming statement is printed on the colored side of the sheet.

This method of use, as previously explained for the graphite sheet, is the same as the alternative one with the granulated sheet.

The difference between the procedure for use explained above and the example below lies in the fact that rubbing the finger on the granulated sheet results in a higher degree of skin exfoliation of the finger compared to stamping it using graphite on the two-faced adhesive-covered sheet. It allows a higher concentration of epithelial cells, thus obtaining a higher quantity of DNA.

Figure 11:
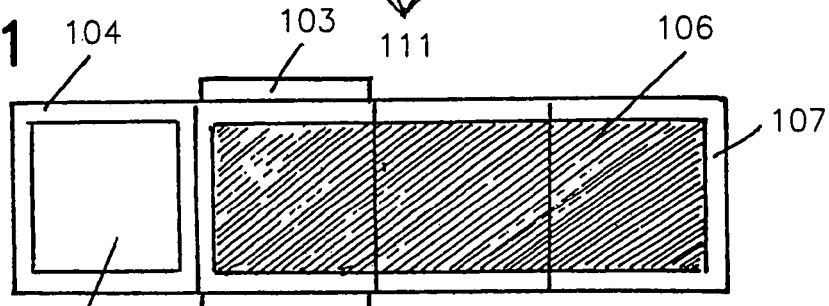
FIG. 11 shows a second embodiment in which the seal is unfolded, and it consists of a seal to stamp the other four fingers.

The alternative process of stamping the other four fingers of the person being identified is similar to the preferred way. In this case, the top and bottom safety flaps are also detached and the four panels of the seal are unfolded: one panel with the polypropylene safety adhesive-covered sheet and three other panels with the graphite or granulated sheet (FIG. 11).

Figure 12:
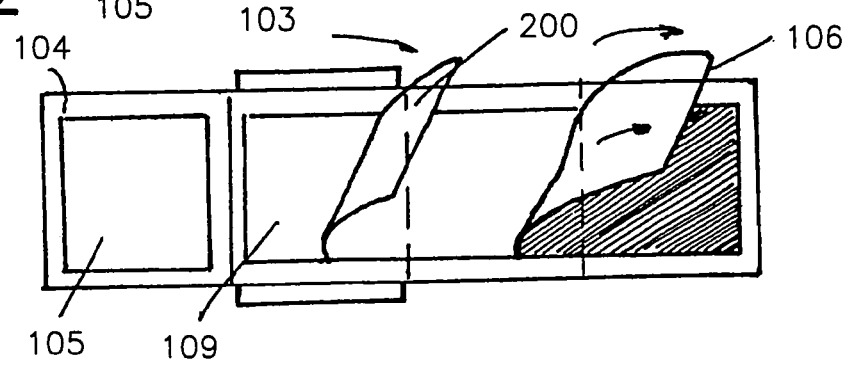
FIG. 12 shows the consecutive steps of the process of using said second embodiment, i.e., firstly, to detach the graphite or granulated sheet and secondly, the silicone protective sheet.
Figure 14:
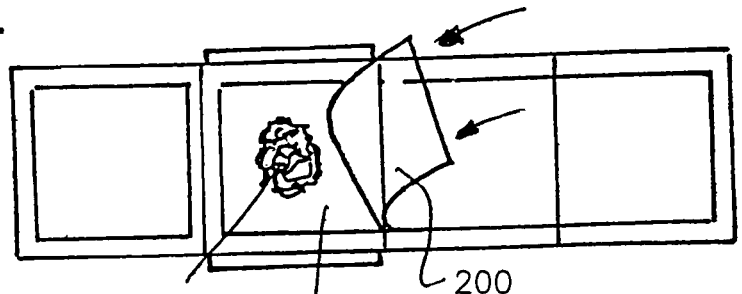
FIG. 14 shows a step consisting of protecting the stamped fingerprints by placing on them the silicone protective sheet previously completely removed or partially detached.
Figure 15:
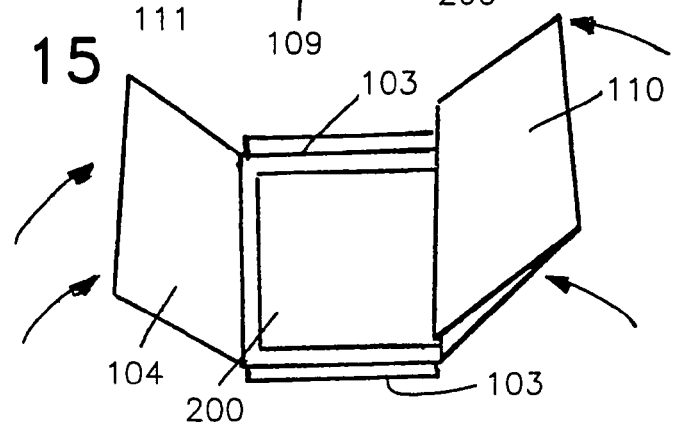
FIG. 15 illustrates the closing process of this alternative embodiment of the safety seal, folding one side over the others.
Figure 16:
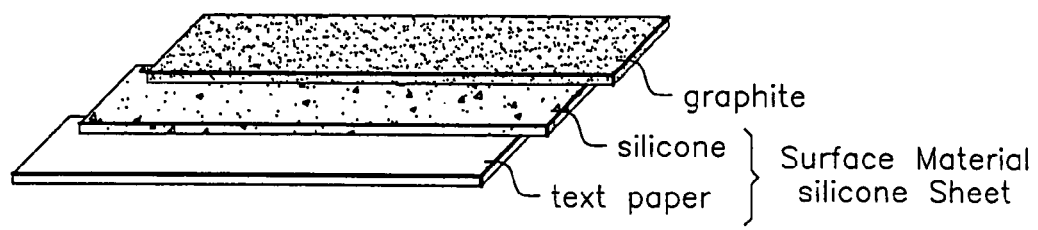
FIG. 16 illustrates the structure of a graphite sheet.
Figure 17:
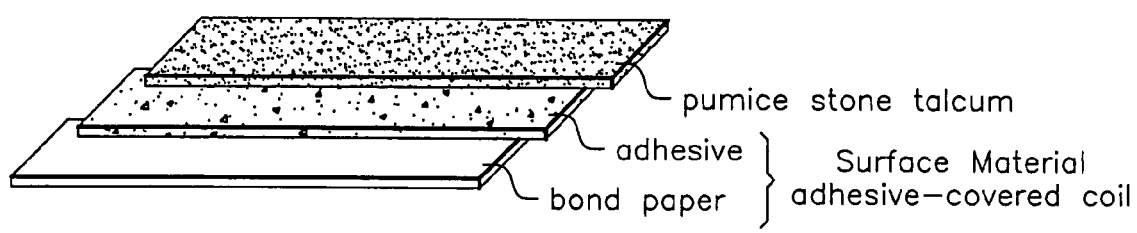
FIG. 17 illustrates the structure of a granulated sheet.

Then, the graphite or granulated sheet and the polypropylene protective sheet with silicone on one side must be detached (FIG. 12). The four fingerprints must be stamped on the space assigned to said purpose (FIG. 13). Then, the same polypropylene protective sheet silicone on one side must be placed again (FIG. 14). The function is to prevent the stamped fingerprints from getting stuck together once the sides of the panel to seal are folded (FIG. 15). This silicone protective sheet can be totally detached and left aside. Then, the process of collecting the fingerprints starts. After that, the protective sheet is re-attached to protect the stamped fingerprints. Alternatively, upon detaching and pulling the protective sheet up, it may not be necessary to remove the sheet completely, given that on the right lateral panel there may be a stopper to prevent the total detachment of the set and its possible loss.

According to the figures attached, the preferred embodiment of the safety seal (1) basically comprises four sheets or basic related components. By "basically comprises four sheets", we mean that, as it will be detailed below, some of these four sheets are composed of several layers or sub-sheets, although they are not visible to the user.

The first sheet (2) is a base support. It is preferably a Kraft-type sheet of paper with a super-calendared glassine type of high strength and a low gram density (flexible) or high gram (90-120 g semi-rigid). The three external sides, including external sides (2a), (10), and the central back side (not shown), does not have a silicone layer, while the internal sides (8), (4), and (7) are covered by silicone.

The second sheet (5) is placed on the center of the seal. It is a polypropylene film with adhesive on one side and is treated for safety printing, preferably in color, to prevent the reuse of the seal or fringe during transport of the seal. The adhesive used may be PSA type of aqueous acrylate or, preferably, other adhesive with higher tack. The second sheet is preferably a 10-20 micron polypropylene film, which is 11 g/m$^2$ gram, 12.5 micron-thick, and 1,400-kg/square inch in tensile strength.

The safety treatment of said film is known as transfer technique. Such technique consists of a first process of photogravure printing with the pertinent security statement and then applying the printing all over the surface of the film.

FIG. 10 shows what happens if a malicious user tries to detach the self-adhesive safety sheet, which is the second sheet (5), from the seal already closed. The graphic security statement of the safety sheet will inevitably be transferred to the external side (2a) of the seal. This will be the evidence that the seal has been broken or manipulated. Thus, a second use of the same seal should not be allowed. The recipient of the seal should acknowledge that the seal has been broken at a certain time during its transportation. More specifically, from the moment the fingerprints were collected and the seal was closed up to when the pertinent department receives it.

The third sheet of this safety seal comprises a graphite or granulated sheet (6) inserted on the lateral internal side (7) of the seal. A user can detach the graphite or granulated sheet and rub one finger on it. Afterwards, the user can stamp the finger on a two-faced adhesive-covered sheet (9) (the fourth sheet as explained below) that is available on said lateral internal side (7), thus leaving a visible or latent fingerprint (11) with all its organic components adhered to the sheet.

The fourth sheet of the seal comprises the adhesive-covered sheet (9) on which the graphite or granulated sheet (6) is mounted. This supporting material comprises a two-faced adhesive on both sides. This sheet is preferably a 10-20 micron polypropylene film treated on both sides (two-faced) with a PSA type adhesive of aqueous acrylate that does not produce allergic reactions, is not thermo-sealable and with high tensile strength. This two-faced sheet (9) has a weight of: 11 g/m$^2$ gram, a thickness of 12.5 micron, and a tensile strength of 1,400-kg/square inch. Its color is preferably crystal white.

The entire set of the safety seal which comprises these four overlapped sheets is completed with two additional elements that are the safety flaps (3) also in polypropylene and with adhesive on one side. These flaps (3) may be initially treated with security printings that help to detect if they were opened or tampered with. If so, the flaps will transfer a warning inscription to the external surface on the top and bottom edges of the seal.

The complete set of the safety seal with incorporated graphite sheet or granulated sheet may be available in different measurements and designs. For hygienic reasons, it could be available in a heat-sealed tearable-layer package. The preferred embodiment illustrated presents a square ornamental aspect whose approximate measurements of the sides range from 50-55 mm. Likewise, according to the user's specific needs, the proposed safety seal can be manufactured with all the alternative possible sheets. For example, the graphite sheet may be on the left side rather than on the right side. The polypropylene (OPP) sheet may be transparent or in different colors. The adhesive of the central sheet may be colored or transparent, etc.

The second alternative embodiment illustrated in FIGS. 11 to 15, are designed to take fingerprints of the other four fingers of the person being identified. This embodiment comprises the same four sheets used in the preferred embodiment, with a fifth separation sheet (200) being added between the graphite sheet (106) and the central sheet (109) with double adhesive.

The configuration of this alternative embodiment is not a triptych like the preferred one, but it has four sides separated in folds that favor the folding of the lateral sides over the central side, which is the one that bears the adhesive-covered safety flaps (103).

Hence, this second alternative embodiment comprises a first sheet (110) having four panels side by side, each panel foldably connected to the next panel, wherein, when the four panels are in the fully extended position, each of the four panels has a silicone treated upper surface (104, 107) facing the same direction; a second sheet (105) adhering to the upper surface (104) of the first base sheet (110) and being treated for safety printing on one of its sides; a third sheet comprising a detachable graphite or granulated sheet (106); a fifth sheet comprising a separation sheet (200) with an upper surface that is not silicone treated and a lower surface that is silicone treated; and a fourth central sheet (109) having adhesives on its upper and lower surfaces, wherein the lower surface of the fourth central sheet (109) adheres to the upper surfaces of the first sheet (110), the lower surface of the separation sheet (200) of the fifth sheet adheres to the upper surface of the fourth central sheet (109), and the detachable graphite or granulated sheet (106) adheres to the upper surface of the separation sheet (200) of the fifth sheet.

On opening the seal and unfolding the four sides of the set, the user will detach the graphite or granulated sheet (106) and rub it on his/her fingers, as in the preferred way. However, he/she must remove the separation sheet (200) that is underneath, to finally place his/her fingerprints (111) on the central sheet (109) with double adhesive.

The graphite or granulated sheet (106) may be detached and completely removed. Alternatively, a sheet may be simply partially detached so as to leave a space for the fingerprint, lining the seal by means placed on one of its corners (107).

The adhesive used, both in this embodiment and in the preferred embodiment, is preferably PSA type that is an acrylate co-polymer in aqueous dispersion.

Lastly, the user must place the separation protective sheet (200) again, by making contact between its backside with the central sheet (109) which bears the stamped fingerprints.

This back side of the separation sheet (200) contacting the adhesive of the two-faced central sheet (109) is treated with silicone, thus preventing both sheets from sticking together and preventing the fingerprints and genetic material collected from deformation or damage.

Although the preferred embodiment is for a single fingerprint (thumb) and the second embodiment is used for the four remaining fingerprints; evidently, if only one seal is necessary to cover the five fingerprints, the second embodiment can be amended by adding an extra panel. In that way five fingerprints can be printed instead of four.

Both processes are designed to collect latent fingerprints on surfaces and to collect fingerprints in situ to people to be identified at a certain time. For example, police staff could use it to identify a person, either being alive or deceased, whose true identity must be checked.

This seal will also be useful for security forces, particularly firemen and police or forensic doctors to collect fingerprints and DNA of people who might have had road accidents or might have committed a crime and do not carry identity cards with them.

In case, for example, the seal were to be used in any of its two embodiments to collect latent fingerprints on certain surfaces, this would be possible by pulling up the graphite or granulated sheet (6, 106) and placing the adhesive-covered surface (9, 109) of the central sheet on the surface where the latent surface might be.

In case of using the alternative process for this task, the separation sheet (200) must also be detached (200).

In both cases, the invention solves the problem of having an inviolable safety seal for the collection and carrying of genetic samples, making it impossible to be manipulated at will or tampered with.

A third embodiment is provided, with the intention to reduce production costs and achieves an economical version, without being less effective.

This third version of the seal comprises only two sheets, eliminating the third sheet (6) (graphite or granulated) and the fourth sheet (9) (with adhesive on two surfaces) of the preferred embodiment.

This embodiment comprises the triptych base sheet and central sheet of polypropylene with adhesive on only one side. The difference is that an adhesive and a fine layer of ground pumice stone grains are spread on one internal surface so that the surface becomes rough or granulated. This is not a detachable or disposable sheet but the rough or granulated surface is a part of the same base sheet on one of the internal lateral sides.

In this case, the genetic material collected is included in the granulated surface and deposited between the micro-interstices generated by the space left between crushed granules of pumice stone. The difference with the previous embodiments is that while the genetic sample adhered to the two-faced adhesive, in this case, it is incorporated into the granulated surface.

Detail of the Structure of the Graphite Sheet:

The graphite sheet (6, 106) incorporated into the two-surfaced sheet (9, 109) of the safety seal, seems to be only one sheet at first sight. However, it is composed of three different layers. The first layer is a text paper. The second layer is made of silicone, and the third layer includes graphite itself.

Description of Component Elements:

The surface material is a piece of silicone text paper over which ground graphite is spread. The text paper is of high strength and density glassine type, with silicone on one side that provides a smooth and semi-glossy finish. The typical gram ranges are from 75 to 85 $g/m^2$, and it may vary according to its application. The thickness is approximately 65-75 mic, according to the type of material. The longitudinal tensile strength is between 15-20 kg/ln, while transversal tensile strength ranges from 7.5-11 kg/ln. The color of the text paper is preferably white. It is presented as 70-75 mm diameter coils.

The graphite layer comprises a safe organic component as from graphite ground as dry-talcum powder.

For that purpose, it has been proven that the provision of a granulated sheet of rough surface facilitates the collection of higher quantity of genetic information given that the dead cells or organic remnants on fingertips are easily detached if they are slightly rubbed with a rough surface as the one of the granulated sheet. For this reason, the present invention provides, as an alternative, a safety seal with the same structural characteristic of the variants detailed previously, with the only difference being that graphite sheet is to be replaced by a granulated sheet, whose characteristics are detailed below.

Detail of the Structure of the Granulated Sheet:

The granulated sheet (6, 106) incorporated to the two-surfaced sheet (9, 109) of the seal, seems to be only one sheet at first sight. However, it is composed of three different layers. The first layer is 50-80 g bond paper. The second layer is PSA adhesive. The third one is a layer of fine pumice stone grains.

Description of Component Elements:

The surface material is a piece of adhesive-covered bond paper over which fine grains of ground pumice stone are spread. The bond paper has high strength and density, with adhesive-covered on one side. The typical gram ranges from 50 to 80 g/m2 (it may vary according to its application. The thickness is approximately 30-50 mic. The longitudinal tensile strength is between 10-15 kg/ln, while transversal tensile strength ranges from 7.5-10 kg/ln. The color of bond paper is preferably white. It is presented as 70-75 mm diameter coils.

The pumice stone grains comprise a safe organic component derived from the pumice stone being ground as a dry granulated powder.

The embodiment of the seal with incorporated granulated sheet is useful for the cases in which a higher quantity of DNA is required, since by rubbing the finger on the granulated sheet, a higher degree of skin exfoliation of the finger rubbed will be obtained. By stamping it in a latent way, without using graphite, on the two-surfaced adhesive-covered sheet, a higher concentration of epithelial cells will be obtained.

On implementing the safety seal exemplified and described, modifications and/or variants of the embodiments may be introduced. All of which must be considered within the scope of protection of the present invention.

The invention claimed is:

1. A non-intrusive portable safety seal to collect DNA and genetic patterns of people, characterized in that it comprises:
   a first sheet being a triptych having a central panel defined by top, bottom and opposite side edges, and a first side panel and a second side panel each connected to one of the opposite side edges and being foldable over the central panel, wherein, when the triptych is in the fully extended position, each of the central panel, the first side panel and the second side panel has a silicone treated upper surface facing the same direction;
   a second sheet adhering to the upper surface of the first sheet and being treated for security printing on one of its surfaces;
   wherein the upper surface of the first side panel or the second side panel has adhesive applied thereon and a fine layer of ground pumice stone grain spread on the adhesive so that the surface becomes rough or granulated.

2. A non-intrusive portable safety seal to collect DNA and genetic patterns of fingerprints, characterized in that the seal comprises:
   a first sheet being a triptych having a central panel defined by top, bottom and opposite side edges, and a first side panel and a second side panel each connected to one of the opposite side edges and being foldable over the central panel, wherein, when the triptych is in the fully extended position, each of the central panel, the first side panel and the second side panel has a silicone treated upper surface facing the same direction;
   a second sheet adhering to the upper surface of the first sheet and being treated for safety printing on one of its surfaces;
   a third sheet comprising a detachable graphite or granulated sheet; and
   a fourth sheet that comprises an adhesive-covered sheet on both surfaces, wherein one surface of the adhesive-covered sheet adheres to the upper surface of said first sheet, and the other surface of the adhesive-covered sheet adheres to the third sheet.

3. The portable safety seal, according to claim 2, characterized in that the seal further comprises two safety flaps preferably of polypropylene with adhesive on one surface and the safety flaps being connected to the top and bottom sides edges of the central panel, respectively.

4. The portable safety seal, according to the claim 3, characterized in that said flaps have a security treatment to detect if they were opened or tampered with by transferring a warning inscription to the external surface on the top and bottom edges of the seal when the flaps are opened or tampered with.

5. The portable safety seal, according to claim 2, characterized in that the second sheet is preferably a polypropylene film that has adhesive on one surface.

6. The portable safety seal, according to claim 2 characterized in that the adhesive-covered sheet on both surfaces is preferably a polypropylene film.

7. A non-intrusive portable safety seal to collect DNA and genetic patterns of fingerprints, in that the seal comprises:
   a first sheet having a series panels side by side, each panel foldably connected to the next panel, wherein, when the panels are in the fully extended position, each of the panels has a silicone treated upper surface facing the same direction;
   a second sheet adhering to the upper surface of the first base sheet and being treated for safety printing on one of its sides;
   a third sheet comprising a detachable graphite or granulated sheet;
   a fifth sheet comprising a separation sheet with an upper surface that is not silicone treated and a lower surface that is silicone treated; and
   a fourth central sheet having adhesives on its upper and lower surfaces, wherein the lower surface of the fourth central sheet adheres to the upper surface of the first sheet, the lower surface of the separation sheet of the fifth sheet adheres to the upper surface of the fourth central sheet, and the detachable graphite or granulated sheet adheres to the upper surface of the separation sheet of the fifth sheet.

8. The portable safety seal, according to claim 7, characterized in that it further comprises safety flaps preferably of polypropylene and with adhesive on one of its surfaces wherein the safety flaps are connected to a top side edge and a bottom side edge of the central panel of the first sheet, respectively, and said top and bottom sides edges are not the side edges connecting other panels.

9. The portable safety seal, according to the claim 8, characterized in that said flaps may have a security treatment to detect if they were opened or tampered with by transferring a warning inscription to the external surface on the top and bottom edges of the seal when the flaps are opened or tampered with.

10. The portable safety seal, according to claim 7 in that the second sheet is preferably a polypropylene film that has adhesive on one surface.

11. The portable safety seal, according to claim 7, characterized in that the adhesive-covered sheet is preferably a polypropylene film.

* * * * *